(12) United States Patent
Aldridge et al.

(10) Patent No.: US 6,675,629 B2
(45) Date of Patent: Jan. 13, 2004

(54) METHOD OF AND INSTRUMENT FOR ANALYZING A GAS

(76) Inventors: Roland Aldridge, 225 E. Hillcrest Blvd., Monrovia, CA (US) 91016; Steven Kirchnavy, 27391 Morro Dr., Mission Viejo, CA (US) 92692

( * ) Notice: Subject to any disclaimer, the term of this patent is extended or adjusted under 35 U.S.C. 154(b) by 0 days.

(21) Appl. No.: 10/106,635

(22) Filed: Mar. 26, 2002

(65) Prior Publication Data

US 2003/0182988 A1 Oct. 2, 2003

(51) Int. Cl.[7] ............................ G01N 4/00; G01N 35/00
(52) U.S. Cl. ..................... 73/1.07; 73/1.06; 73/23.2; 73/864.81; 73/864.83; 73/864.85
(58) Field of Search ....................... 73/1.03, 1.06, 73/1.05, 864.81, 864.84, 864.85, 864.83, 23.2, 31.07

(56) References Cited

U.S. PATENT DOCUMENTS

| | | | | |
|---|---|---|---|---|
| 4,101,282 A | * | 7/1978 | Ririe | 422/93 |
| 4,597,285 A | * | 7/1986 | Kuchar et al. | 73/24.04 |
| 4,738,147 A | * | 4/1988 | Tomlin | 73/864.81 |
| 4,947,339 A | * | 8/1990 | Czekajewski et al. | 702/24 |
| 5,054,309 A | * | 10/1991 | Mettes et al. | 73/1.03 |
| 5,355,781 A | * | 10/1994 | Liston et al. | 99/476 |
| 5,597,535 A | * | 1/1997 | Schaedlich et al. | 422/88 |
| 5,728,289 A | | 3/1998 | Kirchnavy et al. | |
| 5,739,038 A | * | 4/1998 | Burrows | 436/113 |
| 6,029,499 A | * | 2/2000 | Sittler et al. | 73/23.42 |
| 6,207,460 B1 | * | 3/2001 | Kishkovich et al. | 436/106 |

* cited by examiner

Primary Examiner—Michael Cygan
(74) Attorney, Agent, or Firm—John J. Connors; Connors & Associates, Inc.

(57) ABSTRACT

An instrument provides a quantitative measurement of an analyte in a gas. It includes a detection cell that provides an indication of an amount of analyte present in the gas, and a valve having a closed position, a sample gas position, and a calibration gas position. There is a calibration gas inlet orifice in communication with a gas outlet through a first flow path including the valve and the detection cell, and a sample gas inlet orifice in communication with the gas outlet through a second flow path including a scrubber, the valve, and the detection cell. Two orifices of different sizes, a sample gas orifice along the second flow path, and a bypass orifice positioned between the sample gas orifice and the gas outlet, prevent a build up of excessive pressure in the instrument when the valve is in the closed position or the calibration gas position.

61 Claims, 10 Drawing Sheets

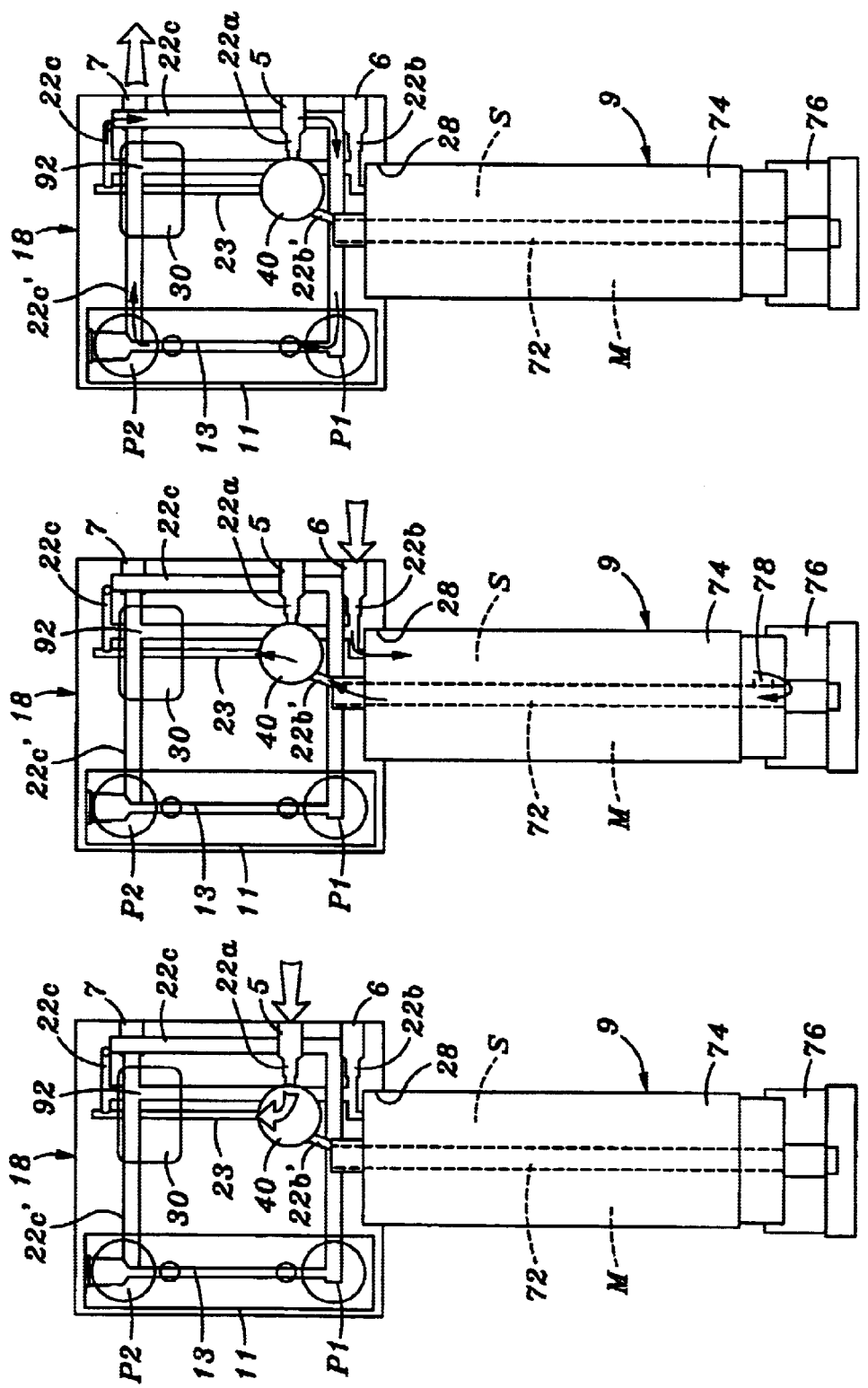

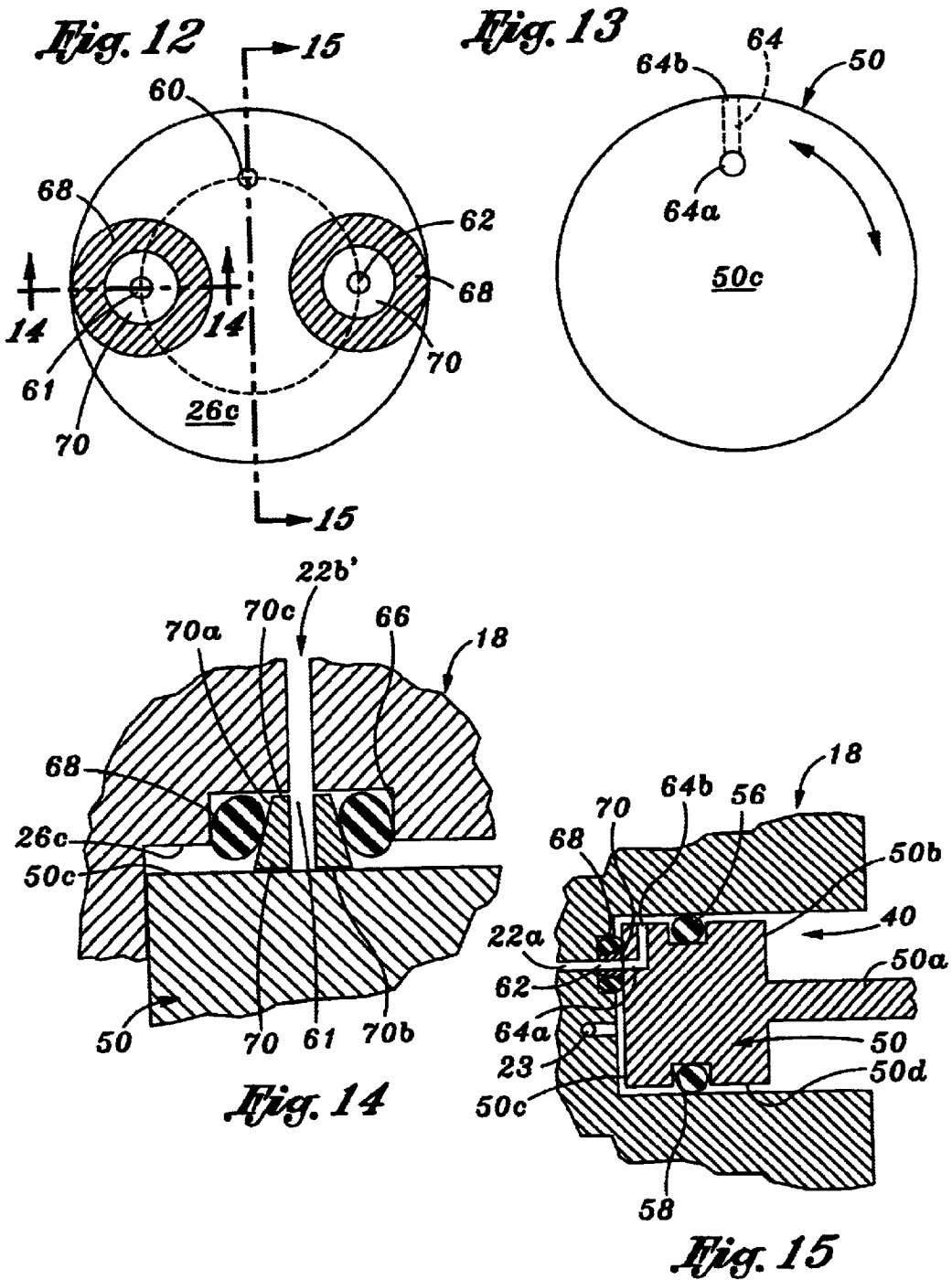

METHOD OF AND INSTRUMENT FOR ANALYZING A GAS

INCORPORATION BY REFERENCE

Applicants incorporate herein by reference any and all U. S. Patents, U. S. Patent Applications, and other documents and printed matter cited or referred to in this application.

BACKGROUND OF INVENTION

It is common practice to analyze gases to determine the quantitative level of certain constituents (herein analytes) of the gas. Frequently, gases are analyzed for their oxygen content, particularly methane from coal or gas wells. The higher levels of oxygen in methane gas lead to corrosion of pipe lines and also may present a danger of explosion. When oxygen levels exceed, for example, 20 parts per million (ppm), an alarm or signal is given which is used to shut down the flow of methane from a well being monitored.

The instrument used to perform such analysis typically includes an assembly of discrete components including valves, valve fittings, flow meters, scrubbers, pressure regulators, needle valves, etc. Because of the numerous components, these instruments are very bulky, taking up space which could be utilized for better purposes. Most, if not all, of these discrete components are connected by tubing. The connections are prone to leak, particularly if they have to be broken and remade. Typically, the scrubber employed contains a material that removes deleterious constituents from the sample gas. This scrubber material changes color when exhausted and consequently needs to be replaced frequently, requiring disconnection of at least some of the components.

SUMMARY OF INVENTION

This invention has several features. Without limiting the scope of this invention as expressed by the claims that follow, its more prominent features will now be discussed briefly. After considering this discussion, and particularly after reading the section entitled, "DETAILED DESCRIPTION," one will understand how the features of this invention provide its benefits, which include, but are not limited to, compactness, ease of assembly of components, ease of replacement of components when required, minimization of disconnection of components, and avoidance of leakage from or into the instrument.

The first feature of the gas analyzer instrument of this invention is that it includes a block having a sample gas inlet, a calibration gas inlet, and a gas outlet. Typically, the block has a height of from 3 to 4 inches, a width of from 3 to 4 inches, and a depth of from 1 to 3 inches. A valve and a detection cell are mounted to the block, with the cell being mounted in a manner that allows the gas being analyzed to flow past it. Typically, the detection cell is seated within a cavity in the block. The valve has a closed position, a sample gas position, and a calibration gas position. With the valve in the closed position or the calibration gas position, essentially all of the sample gas exits the gas outlet. With the valve in the sample position, a portion of the sample gas flows past the detection cell. The block includes (1) a first passageway extending from the calibration gas inlet through the valve and past the detection cell to the gas outlet, (2) a second passageway extending from the sample gas inlet through the valve and past the detection cell to the gas outlet, and (3) a third passageway that is in communication with the gas outlet.

The second feature is the use of a sample gas orifice and a bypass orifice. A calibration gas orifice may also be employed. The sizes of these orifices may vary, and in some instances within the same instrument, they have different sizes depending upon the application and environment under which the instrument is being used. The sample gas orifice is along the second passageway upstream of the valve, and the bypass orifice is along the third, passageway downstream of the sample gas orifice. As sample gas is being introduced through the sample gas inlet when the valve is in the sample gas position, at least a portion of the sample gas flows through the third passageway and exits the gas outlet. The size of the orifices is important for controlling the flow rate of gas through the instrument within a selected flow rate range over a variable gas inlet pressure over a given range. In a preferred embodiment of this invention, the gas introduced through either the sample gas inlet or the calibration gas inlet is within the range from 1 to 100 pounds per square inch gage (psig), and the orifices are sized so that the flow rate of gas through the instrument is within a predetermined range from 0.5 to 7 standard cubic feet per hour. Under these parameters, the orifices have an area from 0.00001 to 0.0005 square inch. When these orifices are substantially circular, they have a diameter from 0.004 to 0.022 inch.

In a preferred embodiment, the sample gas orifice is always in communication with the gas outlet through the bypass orifice regardless of the position of the valve. Consequently, at least a portion of the sample gas always exits the gas outlet as long as sample gas flows into the sample gas inlet. In one preferred embodiment of this invention, the instrument is designed so that most of the gas entering the instrument flows past the detection cell. This is not, however, critical. In some cases, particularly where it is desired to minimize the lag time between sampling a gas stream and testing of the sampled gas, most of the sample gas entering the instrument flows through the bypass orifice and out the gas outlet, and only a minor portion flows past the detection cell. In another case where it is desired to minimize the amount of sample gas being tested, most of the sample gas flows past the detection cell. In this case, the bypass orifice has a predetermined size that is substantially greater than the predetermined size of the sample gas orifice, preferably, the area of the bypass orifice is at least two times greater than the area of the sample gas orifice.

The third feature is that a scrubber is attached to the block upstream of the detection cell and down stream of the sample gas orifice. The scrubber removes from the sample gas unwanted substances, particularly those that have a deleterious effect on the cell. The scrubber comprises a see-through container made of either a transparent or translucent material. This see-through container holds scrubber material that removes the unwanted substances and changes color to indicate that the scrubber material is exhausted and needs replacement. The container is mounted to be detached from the block to provide access to the scrubber material to replace exhausted material. Preferably, there is a filter between the valve and the scrubber. The sample gas orifice and bypass orifice are also sized to maintain the pressure within the scrubber when the valve is in the closed position or the calibration gas position at a reduced pressure substantially below the elevated inlet pressure of the gas being analyzed, preventing a build up of excessive pressure in the scrubber when the valve is in either the closed position or the calibration gas position.

The fourth feature is that, in a preferred embodiment of this invention, gas leaves the block and then subsequently re-enters the block. In this embodiment, the second passageway has a first branch extending from the sample gas orifice through the block to a first outlet and a second branch extending from a first inlet through the valve and the detection cell to the gas outlet. The scrubber is connected between the first outlet and the first inlet to enable the sample gas to flow through the scrubber prior to flowing through the valve and past the detection cell. The sample gas orifice is along the first branch of the second passageway upstream of the first outlet. The bypass orifice is also upstream of the first outlet.

The fifth feature is that the instrument includes multiple flow paths. The calibration gas orifice is in communication with the gas outlet through a first flow path including the valve and the detection cell, and the sample gas orifice is in communication with the gas outlet through a second flow path including the scrubber, the valve, and the detection cell. The sample gas orifice is along the second flow path, and the bypass orifice is positioned between the sample gas orifice and the gas outlet, allowing a portion of the sample gas to exit the gas outlet. The first flow path and second flow path each includes a common flow path downstream of the detection cell. This common flow path has a first branch that extends through the block between the detection cell and an entrance port of a flow meter and a second branch between an exit port of the flow meter and the gas outlet. The second flow path includes a third branch that extends through the block from the sample gas inlet through the sample gas orifice to an entrance port of the scrubber and a fourth branch that extends through the block from an exit port of the scrubber to the valve.

The sixth feature is that the valve has a unique structure. It includes a cylindrical rotary member mounted within a cylindrical cavity in the block to rotate between the closed position, the sample gas position, and the calibration gas position. The rotary member has a side wall terminating at an inner face surface and a gas conduit extending between the rotary member's inner face surface and the rotary member's side wall. The inner face surface is perpendicular to the longitudinal axis of the cylindrical rotary member. The gas conduit terminates at one end in a first opening on the rotary member's inner face surface and at another end in a second opening on the rotary member's side wall. The cavity has a side wall terminating at a sunken face surface, and this sunken face surface has therein a first aperture in communication with the detection cell through the first passageway. There is a second aperture in the sunken face surface in communication with the scrubber through the second passageway, and a third aperture in communication with the calibration gas orifice through the third passageway. When in the sample gas position, the rotary member's inner face surface covers the third aperture to prevent communication between the calibration gas orifice and the detection cell. When in the calibration gas position, the rotary member's inner face surface covers the second aperture to prevent communication between the scrubber and the detection cell. When in the closed position, the rotary member's inner face surface covers both the second aperture and the third aperture to prevent any gas from flowing past the detection cell. There are seal members surrounding the second and third apertures that bear against the inner face surface of the rotary member.

Other features include the use of a flow meter and a heater. The flow meter is mounted to an exterior surface of the block and is downstream of the detection cell. It has an exit port in communication with the gas outlet through a fourth passageway in the block that by passes the detection cell. The flow meter is in communication with the sample gas orifice, the calibration gas orifice, and the gas outlet in a manner that allows gas to flow through the flow meter prior to exiting the block through the gas outlet. The heater is mounted to the block, preferably within a cavity. A thermistor, connected in a control circuit for the instrument and mounted to the block next to the heater, compensates for the variation in cell output with temperature.

This invention also includes a method of measuring the amount of analyte in a sample gas. This method includes the steps of (a) passing the sample gas by a detection cell mounted in a block having a plurality of passageways therein that direct the flow of gas between a gas inlet and a gas outlet, (b) passing a calibration gas by the detection cell for calibration of said cell, said calibration gas flowing at least in part through a different passageway than the sample gas, (c) controlling which passageway gas flows through by a valve mounted in the block and moveable between a first position when the calibration gas is to flow between the gas inlet and gas outlet and a second position when the sample gas is to flow between the gas inlet and gas outlet, and (d) providing in the block a sample gas orifice along one passageway, and a bypass orifice in the block along another passageway positioned between the sample gas orifice and the gas outlet that allows a portion of the sample gas to exit the gas outlet when the valve is in the first position, said orifices being sized so that, with gas entering the instrument at an inlet orifice pressure within a predetermined range, the flow rate of gas through the instrument is within a predetermined range.

DESCRIPTION OF DRAWINGS

A preferred embodiment of this invention, illustrating all its features, will now be discussed in detail. This embodiment depicts the novel and non-obvious gas analyzing instrument and method of this invention as shown in the accompanying drawings, which are for illustrative purposes only. These drawings includes the following figures (FIGS.), with like numerals indicating like parts:

FIG. 7 is a schematic diagram showing the flow path of the calibration gas into the instrument of this invention and to the detection cell.

FIG. 8 is a schematic diagram showing the flow path of the sample gas into the instrument of this invention, through the scrubber and to the detection cell.

FIG. 9 is schematic diagram showing the common flow path of the calibration gas and sample gas as they as they flow past the detection cell, through the flow meter, and exit the instrument of this invention through the gas outlet.

FIG. 12 is a sectional view taken along line 12—12 of FIG. 6 showing the sunken face surface of the cavity in the block in which the valve rotor is seated.

FIG. 13 is a sectional view taken along line 13—13 of FIG. 4 showing the valve rotor's inner face surface.

FIG. 14 is a sectional view taken along line 14—14 of FIG. 12.

FIG. 15 is a sectional view taken along line 15—15 of FIG. 12.

DETAILED DESCRIPTION

Figure 1:
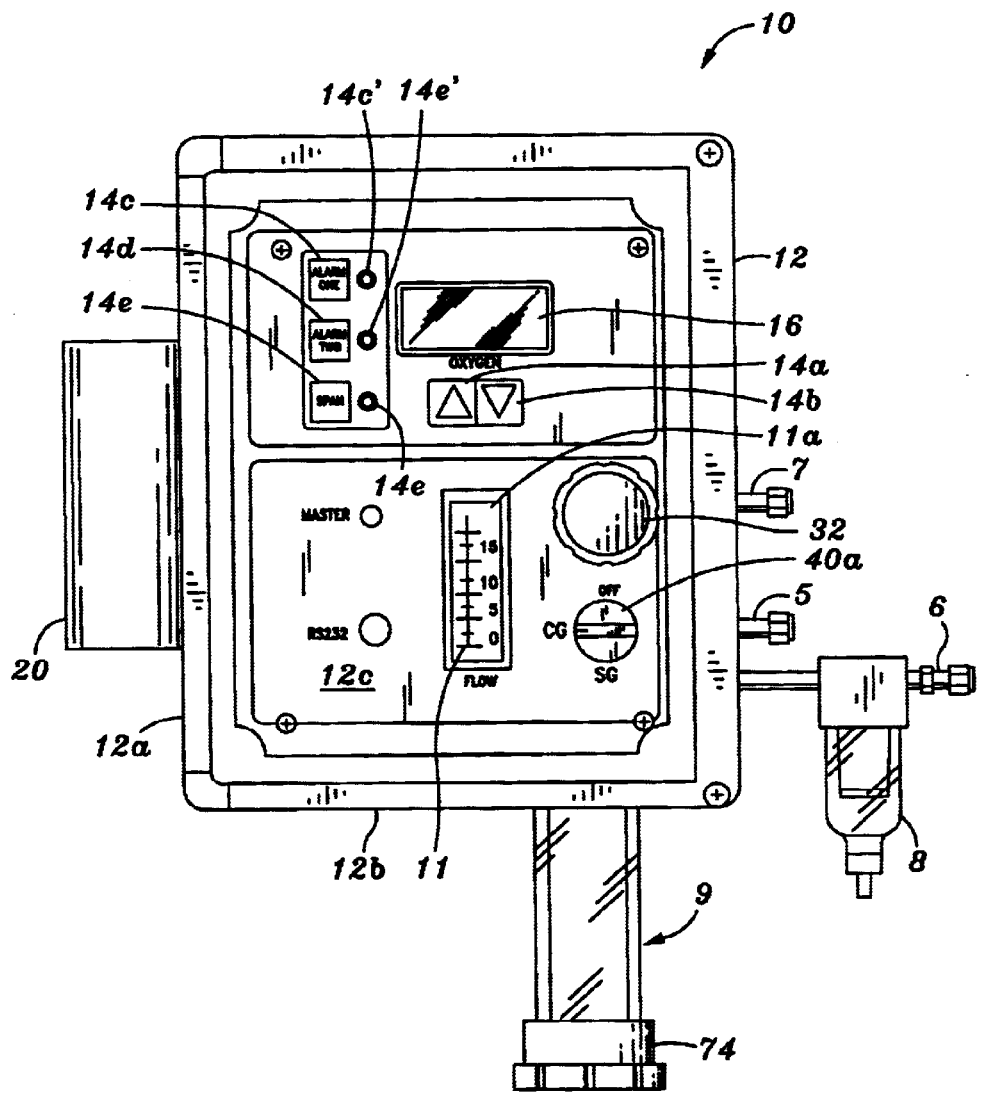
FIG. 1 is a front elevational view of the gas analyzer instrument of this invention.
Figure 2:
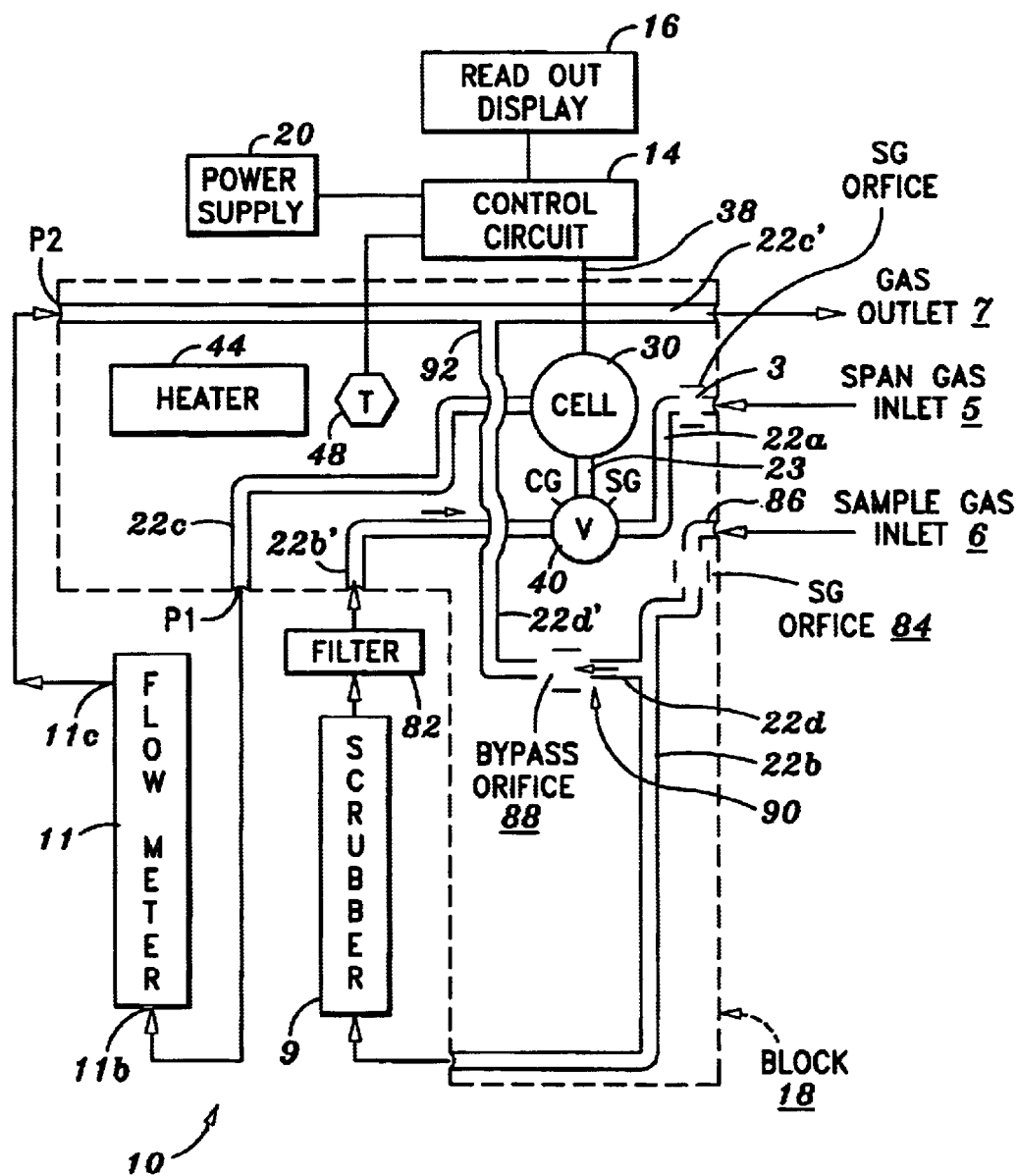
FIG. 2 is a schematic diagram of the gas analyzer instrument shown in FIG. 1.
Figure 3:
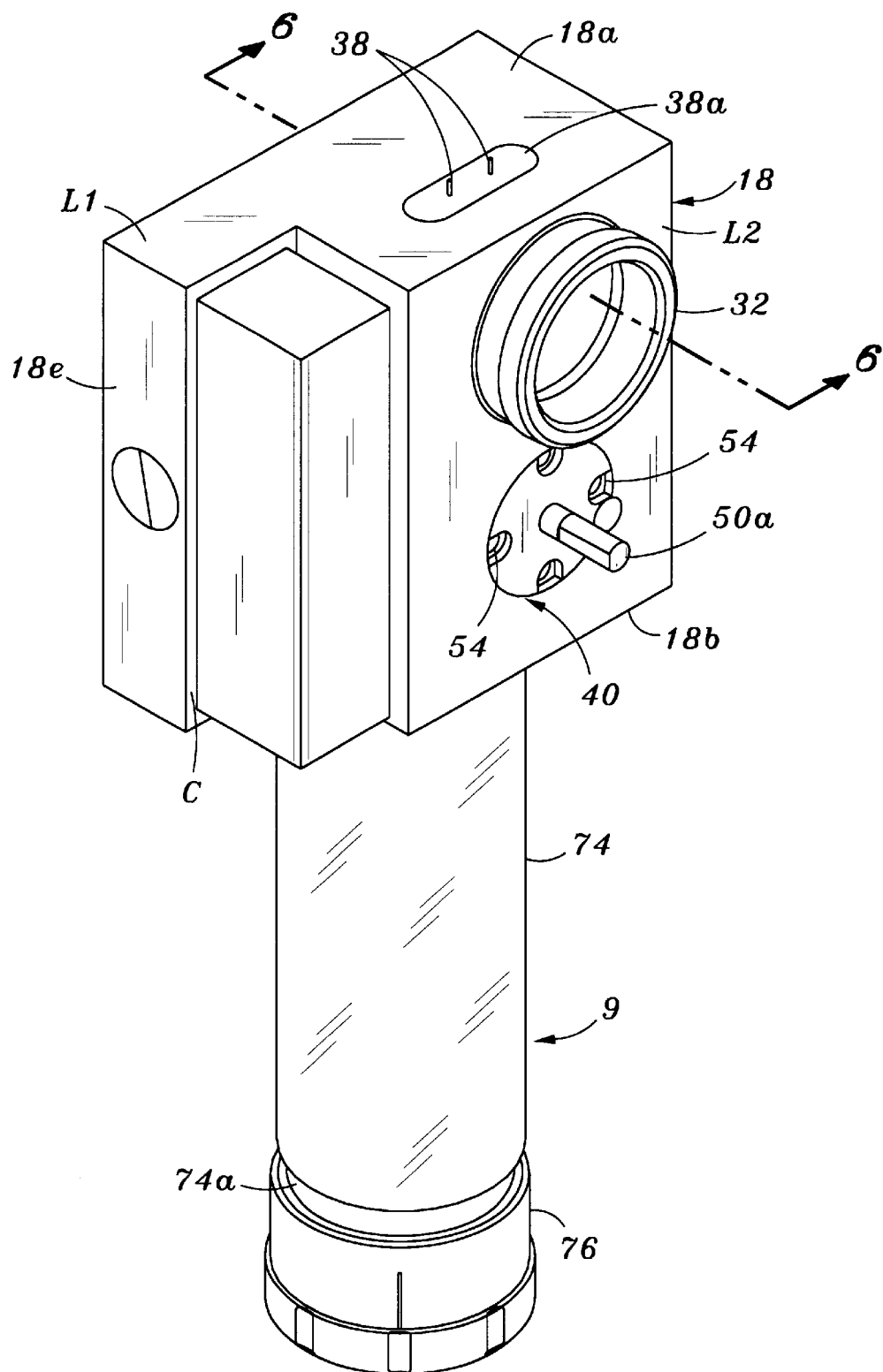
FIG. 3 is a perspective of the block used in the gas analyzer of this invention having a scrubber and a flow meter attached to the block.

As shown best in FIGS. 1 and 2, the instrument 10 of this invention includes a case 12 enclosing a control circuit 14 for the instrument and a block. 18 made of metal such as, for example, nickel plated aluminum. Preferably, the block is drilled to create the inlets, outlets, cavities and passageways needed as discussed subsequently in detail, and any unnecessary openings are filled with gas-tight stoppers. A more expensive technique, would employ a casting technique to form the inlets, outlets, cavities and passageways needed.

Mounted to the block 18 (FIG. 2) are a scrubber 9, a flow meter 11(FIG. 2), a detection cell 30 (FIG. 2), and a valve 40. The control circuit 14 includes a liquid crystal display 16 and buttons 14a through 14e on the front 12c of the case 12. Mounted on a side 12a of the case 12 is an external power supply 20 for the control circuit 14. The buttons 14a through 14e enable a user to set the range over which the instrument 10 measures an analyte in a gas sample (GS), as well as allowing calibration and alarm setting. The user may inspect the instrument settings by pressing the relevant buttons 14a through 14e, whereas to alter the settings, the user must first press both buttons 14a and 14b simultaneously, and then whichever of the buttons 14a through 14e needed to accomplish the desired change. There are potentiometers (not shown) in the control circuit 14 associated with each of the buttons 14c through 14e that each have a manually adjustable set screw 14c', 14d', and 14e' respectively for setting the value of each individual potentiometer. These potentiometers have no effect on the instrument operation unless both the buttons 14a and 14b have been simultaneously pressed, and then only when buttons 14c, 14d or 14e are pressed will its associated potentiometer be effective. The amount of analyte in a gas is shown in engineering units, such as ppm, on the display 16 no matter which range has been selected, although the output voltage may no longer represent the sample concentration if it is outside the value of the selected output range. If the amount of analyte is outside the selected range, the user simply changes the range by manipulation of the buttons 14a and 14b.

The instrument 10 is first calibrated using a calibration gas, commonly referred to as "SPAN" gas. For example, when the instrument 10 is used to analyze a sample gas to determine the amount of oxygen (the analyte) in such sample gas, a calibration gas (CG) is used having therein a known oxygen concentration. By manipulation of the buttons 14a through 14e and adjusting the appropriate set screw 14e', the user sets the readout on the display 16 to correspond to the known concentration of oxygen in the calibration gas introduced into the instrument 10 through a SPAN gas inlet 5 including a calibration gas orifice 3. Subsequent to such calibration, a sample gas (SG) containing an unknown amount of oxygen is introduced into the instrument 10 through a sample gas inlet 6. Both the calibration gas and the sample gas exit the instrument 10 through a gas outlet 7. A coalescing filter 8 filters the sample gas prior to entry into the instrument 10 and removes any condensed moisture and particulates in the sample gas.

The block 18 enables the instrument 10 to avoid using tubing typically employed in conventional analytical instrumentation. As best shown in FIGS. 3 through 9, the block 18 has a generally L-shaped configuration formed by machining a metal cube to provide a corner C between a pair of legs L1 and L2. The block 18 has a topside 18a, bottom side 18b, front side 18c, back side 18d, right side 18e and left side 18f. The block 18 is machined to create gas passageways 22a, 22b, 22b', 22c, 22c', 22d, 2d', and 23 through the block 18 and provide cavities 24, 26, and 28 (FIGS. 4 and 6) within the block having open cylindrical entryways 24a, 26a and 28a, respectively. The cavities 24 and 26 both have their respective entryways 24a and 26a in the front side 18c of the block 18 and the cavity 26 is conveniently located directly beneath the cavity 24. The entryway 28a is in the bottom side 18b of the block 18.

Figure 4:
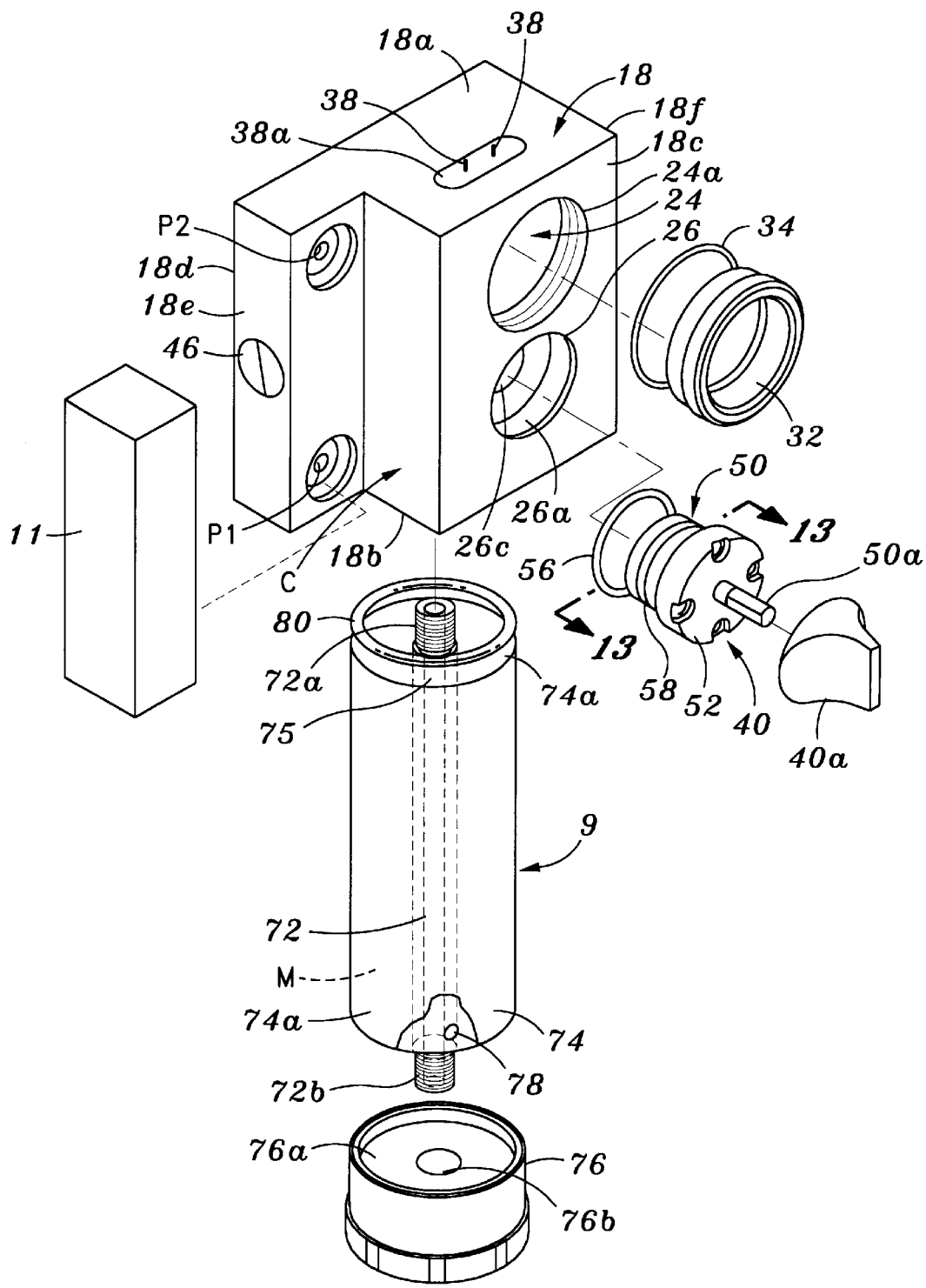
FIG. 4 is an exploded perspective view of the block, scrubber, and flow meter shown in FIG. 3.
Figure 5:
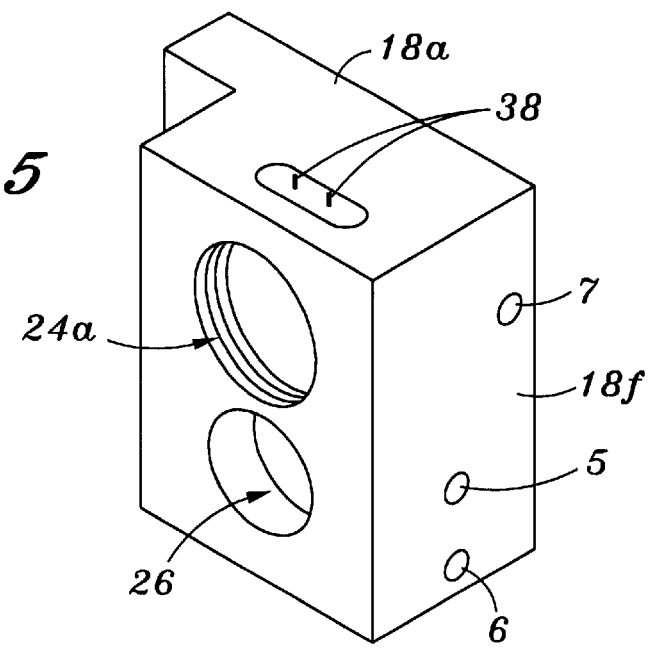
FIG. 5 is perspective view of the block shown in FIG. 3 looking at the side of the block having the calibration gas orifice, sample gas orifice, and gas outlet.
Figure 6:
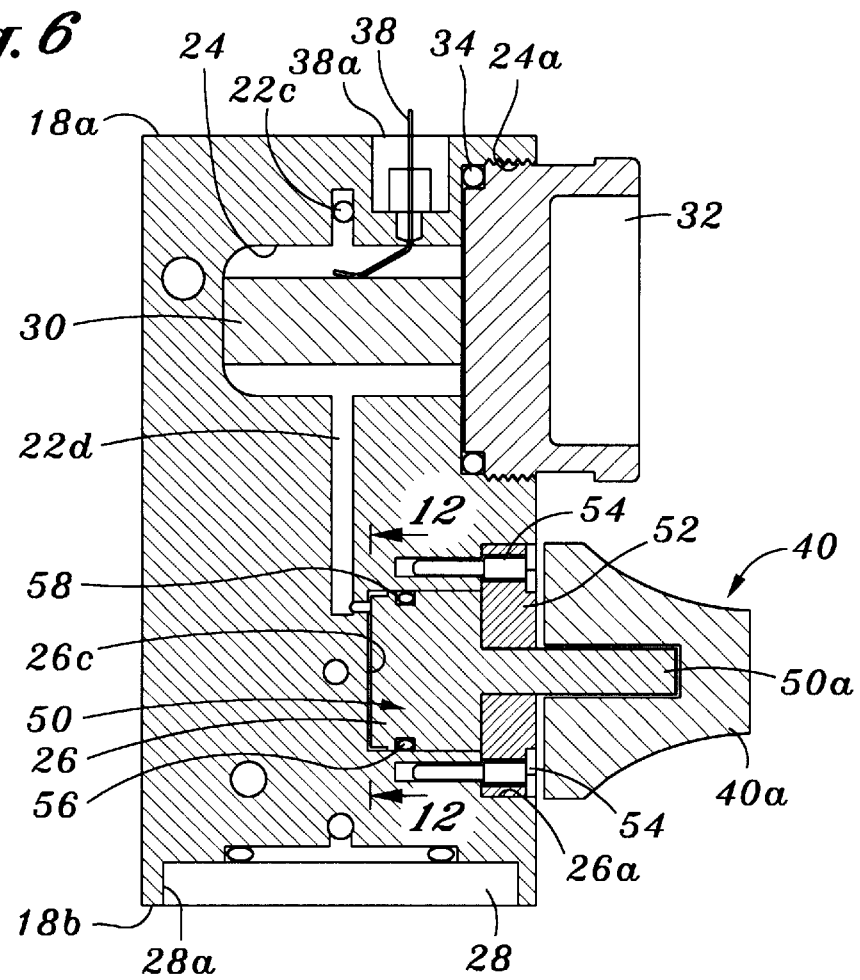
FIG. 6 is a cross-sectional view of the block taken along line 6—6 of FIG. 3.
Figure 10:
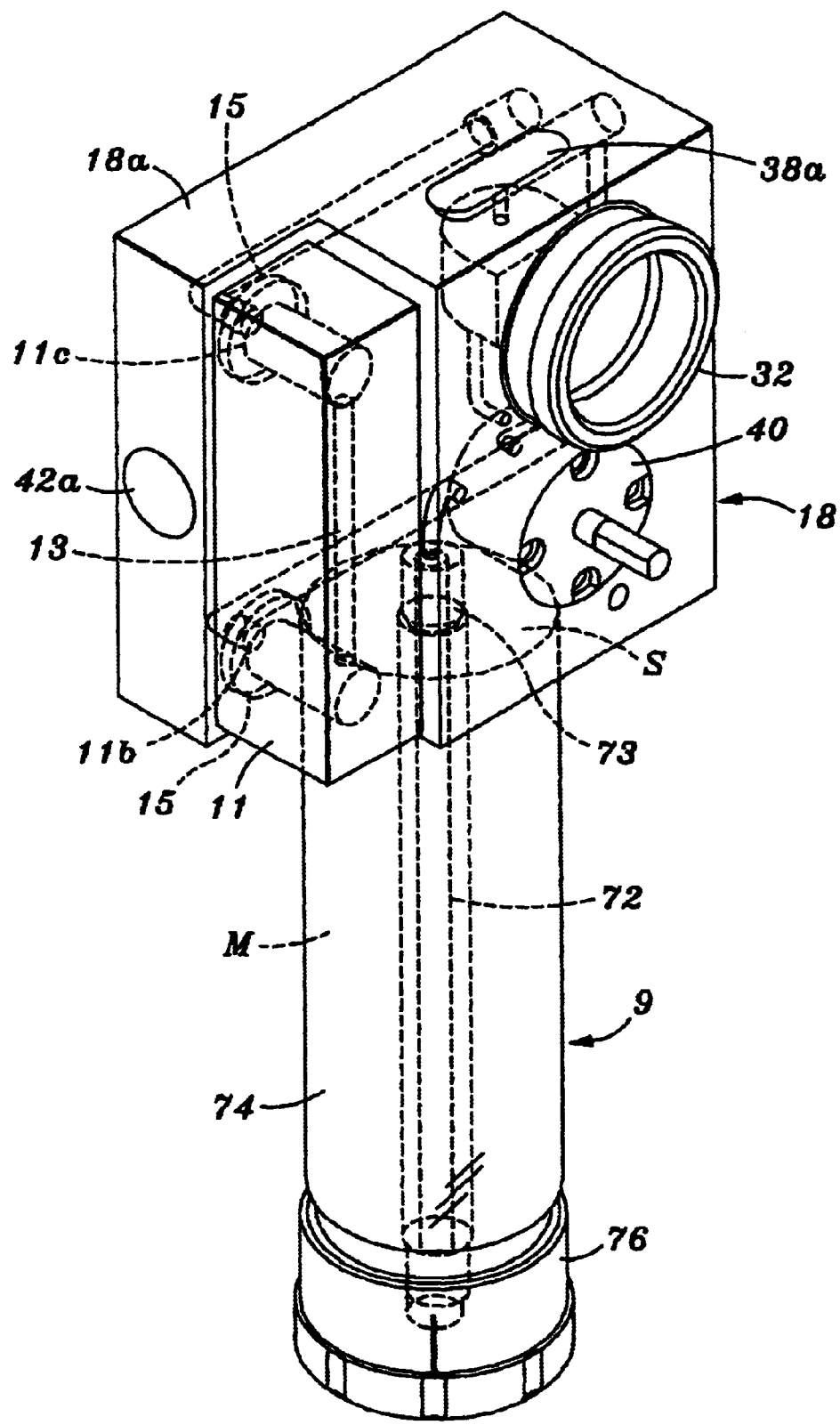
FIG. 10 is a perspective view similar to that shown in FIG. 3 depicting in dotted lines various internal components of the instrument of this invention.
Figure 11:
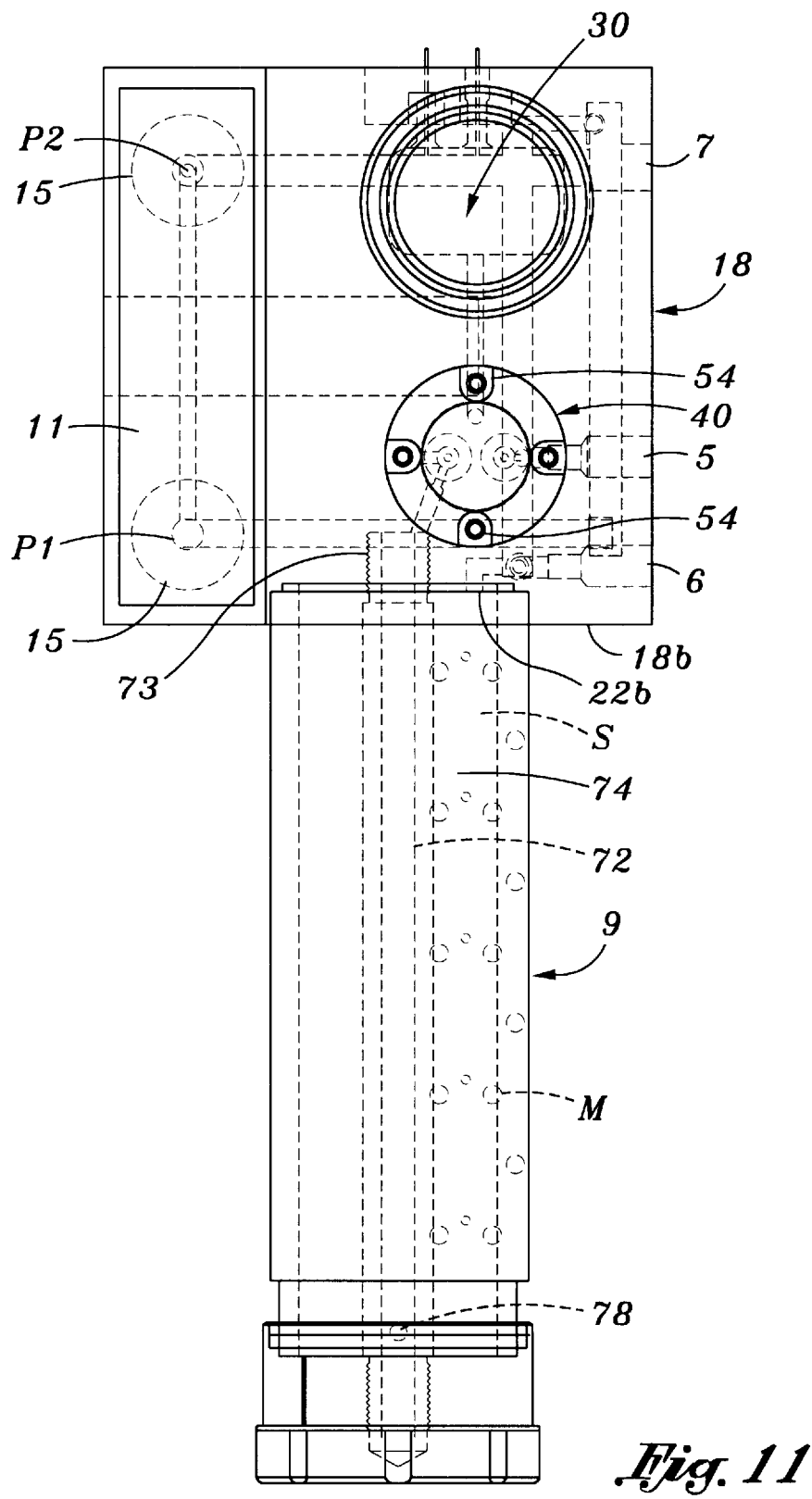
FIG. 11 is a front elevational view of the block with attached scrubber and flow meter depicting in dotted lines various internal components of the instrument of this invention.

As illustrated in FIGS. 1 and 4, the lower portion of the scrubber 9 extends outward from the bottom 12b of the case 12. This scrubber 9 includes an internal hollow tube 72 that has an upper threaded end 72a screwed into a threaded receptacle 73 (FIGS. 10 and 11) in the block 18. The tube 72 is enclosed in a transparent cylindrical pipe 74 and its is concentrically positioned relative to this pipe. Contained within the space S between the tube 72 and pipe 74 is a suitable scrubbing material M used to remove unwanted substances from the sample gas. There is an end cap 76 sealing an open lower end 74a of the pipe 74. The inside surface 76a of the end cap 76 has a central threaded receptacle 76b into which is screwed a lower threaded end 72b of the tube 72. The outside diameter of the pipe 74 is about equal to the diameter of the entryway 28a. Lodged in an annular groove 75 in the face of the entryway 28a is an o-ring 80 that seals the interface between the upper end of the pipe 74 and the entryway 28a. The passageway 22b terminates in the cavity 28 immediately above the space S between the pipe 74 and tube 72, so the sample gas upon entering the scrubber 9 immediately contacts the scrubbing material Near the lower end 72b of the tube 72 is a hole 78 through which sample gas flows after first flowing through the scrubbing material M that removes the unwanted substances from the sample gas as the gas flows through the instrument 10.

A typical unwanted substance is, for example, hydrogen sulfide, a deleterious contaminant frequently present in methane gas being analyzed. A suitable scrubber material for hydrogen sulfide is sold under the name Purafil obtained from The Purafil Corporation. This scrubbing material M changes color as it absorbs hydrogen sulfide gas, gradually changing from its initial bright purple to a gray-brown that indicates that the scrubbing material needs to be removed and replaced. This is accomplished simply by grasping the exterior of the pipe 74 and rotating the entire scrubber assembly to unscrew the upper threaded end 72a of the tube 72 from the threaded receptacle 73. The used scrubbing material is discarded and replaced with fresh material, and the threaded end 72a is screwed back into the threaded receptacle 73 to re-attached the scrubber 9 to the block 18.

Any deleterious substances should be removed from the sample gas prior to the gas flowing into the detection cell 30. This cell 30 generates on contact with gas an electrical signal indicating the amount of analyte present in the gas. A suitable detection cell 30 is sold by Advanced Micro Instruments, Inc. under the designation T-2. The detection cell 30 is seated in the cavity 24, and electrical leads 38 extending through an insulator member 38a seated in the topside 18a of the block 18 connect the cell to the control circuit 14. The entryway 24a to the cavity 24 is threaded and a threaded cylindrical cover 32 is screwed into this entryway 24a, which is about the same diameter as the cover 32. An o-ring 34, near the bottom of the entryway 24a and the inside of the cover 32, seals the cavity 24 to prevent gas from escaping through the interface between the cover 32 and the entryway 24a. A preferred way of mounting the cell 30 is disclosed in U. S. Pat. No. 5,728,289.

The flow meter 11 is attached by screws (not shown) to the exterior of the block 18, fitting into the corner C. A port P1 in the block 18 is aligned with an inlet 11b (FIGS. 2 and 10) in the flow meter 11, and another port P2 in the block 18 is aligned with an outlet 11c in the flow meter 1. There is a channel 13 (FIG. 10) extending between the inlet 11b and outlet 11c. The port P2 is at one end of the passageway 22c'. The other end of the passageway 22c' terminates at the gas outlet 7. O-rings 15 provide seals at the interfaces between the ports P1 and P2 and the inlets 11b and outlet 11c. As depicted in FIG. 1, there is a window 12c in the case 12 enabling the user to observe the flow meter's scale 11a that indicates the flow rate of gas (either sample gas or calibration gas) as it flows through the instrument 10.

Optionally, the instrument 10 may employ a heater 4. The heater 44 may be desired because it is important that water and other vapors present in the sample gas are not allowed to condense within the block 18 and particularly on the cell 30, affecting its performance negatively. There is a heater pocket (FIG. 10) having an opening 42a in the left side 18e in the block 18 that enables the heater 44 (FIG. 4) to be positioned therein. A C-ring 46 (FIG. 4) snaps into the opening 42a to retain the heater 44 within the pocket 42. There is thermistor 48 (FIG. 2) lodged within the block 18 adjacent the heater 44. The thermistor 48 is a component of the control circuit 14. It functions to sense temperature, allowing other electronic devices (not shown) of the control circuit 14 to adjust to compensate for variations in output of the cell 30 with temperature. The control circuit 14 is designed in accordance with well known electronic engineering principles.

The position of the valve 40 establishes the flow path of gas through the instrument 10. The valve 40 has a control knob 40a projecting from the front 12c of the case 12 that the user employs to select one of three valve positions: a calibration gas position CG, a sample gas position SG, and an OFF position. As best illustrated in FIGS. 3, 4, 6, and 12 through 15, the valve 40 includes a cylindrical rotor 50 seated within the cavity 26. A rotor stem 50a projects outward from an exterior side 50b of the rotor 50 through a disk shaped valve retainer plate 52 seated in the entryway 26a, and four screws 54 secure the retainer plate to the block 18. The valve retainer plate 52 holds the rotor 50 in position within the cavity 26, but allows the rotor to be rotated either clockwise or counter clockwise to move it into one of three different valve positions mentioned above. The rotor 50 is preferably made of aluminum, anodized and sealed. A detent mechanism (not shown) including ball detent (not shown) with a detent spring (not shown) may optionally be used to provide a tactile sensation as the user moves the valve 40 into one of the three different positions. The movement of the ball into one of the position, CS, SG or OFF, indicates that the valve 40 is either in the calibration position, sample position, or closed position.

A bottom side 50c of the rotor 50 presses snugly against a substantially flat, sunken bottom wall 26c of the cavity 26. A Buna-n o-ring 56, positioned in an annular groove 58 in the side wall 50d of the rotor 50, provides a seal so that gas cannot escape via the interface between the valve rotor 50 and the cavity entryway 26a. The valve knob 40a is fitted on the stem 50a after the valve retainer plate 52 is attached to the block 18. A gas conduit 64 extends between the bottom side 50c and the side wall 50d of the rotor 50 wall, terminating at one end in an opening 64a on the bottom side 50c and at another end in an opening 64b on side wall 50d.

There are three of spaced apetures 60, 61 nad 62 in the bottom wall 26c of the cavity 26. The apeture 60 is in communication with the detection cell 30 through the passageway 23. The apetuer 61 is in communication with the scrubber 9 through the passageway 22b'. One end of the passageway 22b' terminates at the apeture 61 and the other end of this passageway terminates ast a filter 83 (FIG. 2). This filter 82 is made of sintered metal and is within the upper threaded end 72a of the tube 72. There is a narrow section of the tube 73 next to the thread end 72a containing an o-ring (not shown) that effectively seals the passageway 22b form the cavity 28 so the gas flows from the tube 72 into the passageway 22b' without leakage. The apeture 62 is in communication with the calibration gas orfice 5 through the passageway 22a, which terminates at the apeture 62.

As shown in FIGS. 12, 14, and 15, a recess 66 surrounds each of the apertures 61 and 60. Lodged in each of these recesses 66 is an outer o-ring 68 having a Teflon® washer 70 concentrically seated within the o-ring. An outer wall 70a of the washer 70 tapers inward so that a wider end portion 70b of this washer is pressing against the rotor's bottom side 50c and a narrower end portion 70c fits snug within the o-ring 68. The truncated conical shape of the washers 70 keep the o-rings 68 from being rolled by friction when the valve rotor 50 is rotated. The conical shape of these washers 70 forces the O-rings 68 to attempt to lift the washers, thus stopping them from rolling over the washers. This lengthens the o-ring life and makes a better seal.

FIGS. 7 and 15 show the valve 40 in the calibration gas (CG) position with rotor 50 rotated so that the opening 64a on the rotor's bottom side 50c is aligned with the aperture 62. As depicted best in FIG. 7, calibration gas proceeds along a flow path flowing through the passageway 22a and aperture 62 into the opening 64a and then through the gas conduit 64 and out the opening 64b into the passageway 23 past the cell 30. As shown in FIG. 8, with the valve 40 in the sample gas (SG) position, the rotor 50 has been rotated to align the opening 64a with the aperture 61. Sample gas proceeds along a flow path as follows: First, the sample gas flows along the passageway 22b and out the block 18 and through the scrubber 9 and filter 82 into the passageway 22b'. The sample gas next passes through the aperture 61 and into the opening 64a at the end of the gas conduit 64 and out the opening 64b and into the passageway 23 leading to the cell 30. The opening 64a is only aligned with one of the aperture 61 or 62 at a time. When the valve 40 is in the OFF position, the rotor 50 has been moved so that the opening 64a is displaced away from both the apertures 61 and 62 and the rotor's bottom side 50c covers both these apertures, preventing any flow of gas past the detection cell 30.

As best depicted in FIGS. 2 and 9, upon flowing past the detection cell 30, the gas (either the calibration gas or sample gas) proceeds along the following common flow path: First it flows along the passageway 22c out the port P1 and into the inlet 11b of the flow meter 11. It then flows through the channel 13 and out the flow meter's outlet 11c into the port P2. The gas then flows through the passageway 22c' out the gas outlet 7.

Figure 16:
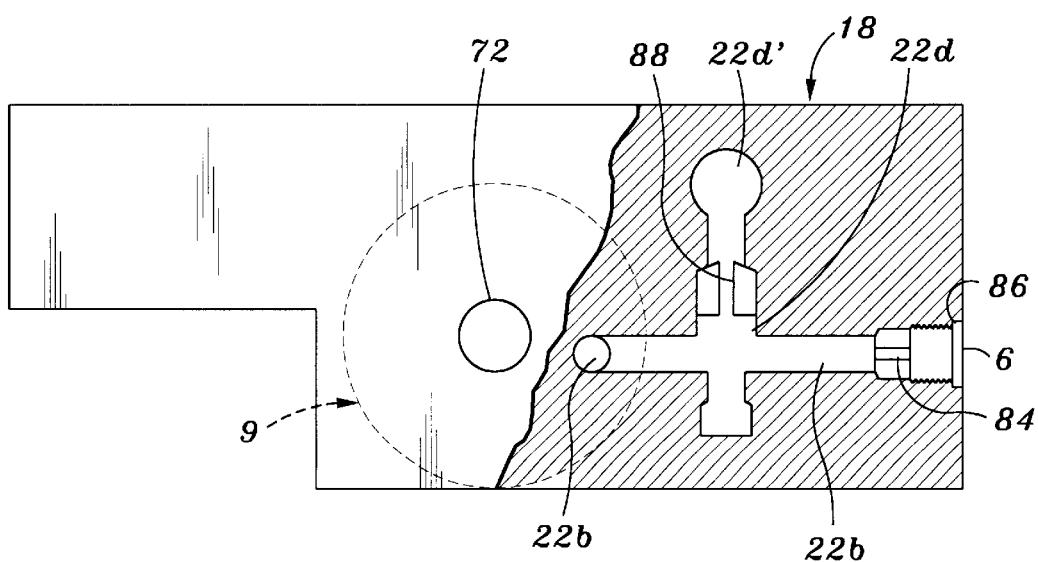
FIG. 16 is a top plan view, with sections broken away, of the block used in the instrument of this invention.
Figure 17:
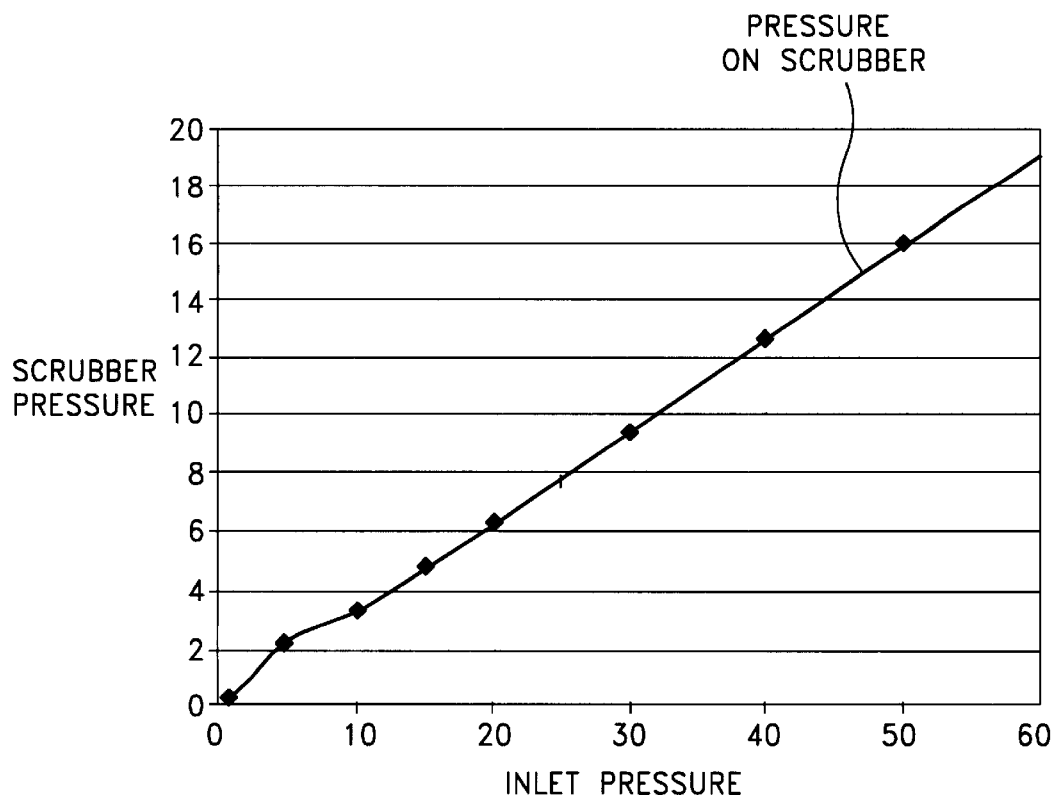
FIG. 17 is a graph showing the relationship of the inlet pressure and downstream pressure in the scrubber.

As illustrated in FIGS. 2 and 16, upon entering the sample gas inlet 6, the sample gas flows through a sample gas orifice 84 in the block 18 at the entry end 86 of the passageway 22b. As the sample gas flows through the sample gas orifice 84, a portion is diverted to flow through the passageway 22d which has a bypass orifice 88 therein located near a junction between the passageways 22d and 22d'. The passageway 22d' extends between the bypass orifice 88 and the passageway 22c', merging with the passageway 22c' at an intersection 92. Thus, a portion of the sample gas is diverted to the gas outlet 7 via the bypass orifice 88 and passageways 22d' and 22c'. Approximately from 5% to 10% volume percent of the sample gas is diverted to the gas outlet 7.

An important feature of this invention is the use of both the sample gas orifice 84 and the bypass orifice 88 to avoid the use of pressure regulators. The sample gas orifice 84 and bypass orifice 88 each have substantially the same length of about ¼ inch. The diameter of the bypass orifice 88 is greater than that of the sample gas orifice 84, preferably so that the area of the bypass orifice is at least 2 times greater than the area of the sample gas orifice 84. Consequently, the area of the bypass orifice 88 is from about twice to about four times greater than the area of the sample gas orifice. In a preferred embodiment, the area of the sample gas orifice 84 is from 0.00001 to 0.0001 square inch, and the area of the bypass orifice 88 is from 0.0001 to 0.0005 square inch. Typically, the area of these orifices 84 and 88 is circular, with the diameter of the sample gas orifice 84 being from 0.004 to 0.012 inch and with the diameter of the bypass orifice being from 0.012 to 0.022 inch. With the valve 40 in the sample gas position, from about 90 to 95 volume percent of the sample gas flows past the detection cell 30.

During normal operation, gas flow is controlled by the sample gas orifice 84. A feature of the orifices is that above a critical pressure, for example 10 psig (pounds per square inch gage), the flow velocity is limited to the speed of sound. Therefore, the mass flow is proportional to the absolute inlet pressure. For example, this means that, if the inlet pressure varies over a range of from 10 to 11 psig, the mass flow will vary over a rate of from about 0.5 to about 2.5 standard cubic feet per hour. The instrument 10 is not sensitive to reading changes over this mass flow rate range. A pressure regulator is therefore not required for normal operation.

When the valve is in the OFF position, sample gas may be introduced into the instrument 10 and this sample gas will flow through the bypass orifice 88 and be vented to the atmosphere through the gas outlet 7. For example, it is important to monitor continually a methane gas well where sample gas is always flowing into the instrument 10. Consequently, when the valve 40 is moved to either the calibration gas (CG) position or the sample gas (SG) position, there will not be a high level of pressure within the scrubber 9. Gas at high pressure within the scrubber 9 could damage the instrument 10 when the valve 40 is moved from the OFF position to the calibration gas (CG) position or sample gas (SG) position, since there is no longer any flow restriction. Because of the relationship between the sample gas orifice 84 and the bypass orifice 88, a build up of pressure within the scrubber 9 is avoided. Consequently, when the valve 40 is in the OFF position or calibration gas (CG) position, (a) the scrubber 9 is not over-pressurized, and (b) upon movement of the valve 40 into the sample gas (SG) position, there is no sudden high flow of gas pass the cell 30. During normal operation, the pressure in the scrubber 9 is very low since it is downstream of the sample gas orifice 84. There are no significant flow restrictions before the gas outlet 7, so the bypass orifice 88 does not allow much sample gas to flow through it in normal operation.

In operation and after calibration, the valve 40 is manually turned to the sample gas (SG) position to allow sample gas to flow into the instrument 10 under the control of the sample gas orifice 84. Because there is a differential in pressure of the instrument 10 (the instrument is at atmospheric pressure) and an elevated pressure of the sample gas, the sample gas flows into the instrument. FIG. 12 shows the relationship between inlet pressure and the downstream pressure in the scrubber 9. At a low differential in pressure, the flow through the sample gas orifice 84 is proportionate to this differential in pressure and inversely proportional to the area. At higher differential pressures, the flow rate gets faster and keeps increasing until the velocity reaches the speed of sound. At this speed, gas velocity cannot increase. However, increase in the upstream pressure of the sample gas, proportionately increases the gas density, and therefore the mass flow through the sample gas orifice 84 increases in direct proportion to the absolute inlet pressure. The changes in downstream pressure, however, have no significant impact on gas flow rate. A typical sample gas orifice 84 is sized so that at an inlet pressure of about 60 psig, a flow rate of about 4 standard cubic feet per hour of sample gas flows through the instrument 10.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiment disclosed. On the contrary, the intention is to cover all modifications and alternate constructions coming within the spirit and scope of the invention as generally expressed by the following claims, which particularly point out and distinctly claim the subject matter of the invention.

What is claimed is:

1. An instrument for analyzing a gas comprising
    a block having a sample gas inlet including an orifice, a calibration gas inlet including an orifice, and a gas outlet,
    a detection cell mounted to the block past which the gas being analyzed flows,
    a valve mounted to the block, said valve having a closed position, a sample gas position, and a calibration gas position,
    a first passageway in the block extending from the calibration gas inlet orifice through the valve and past the detection cell to the gas outlet,
    a second passageway in the block extending from the sample gas inlet orifice through the valve and past the detection cell to the gas outlet, and said sample gas inlet orifice being positioned along the second passageway upstream of the valve, and a third passageway in the block including a bypass orifice downstream of the sample gas inlet orifice, said third passageway being in communication with the gas outlet while sample gas is being introduced through the sample gas inlet orifice when the valve is in the sample gas position, enabling at least a portion of the sample gas to flow through the third passageway and exit the gas outlet, said orifices being sized so that, with gas entering the instrument at an inlet orifice pressure within a predetermined range, the flow rate of gas through the instrument is within a predetermined range.

2. The instrument of claim 1 where the predetermined inlet orifice pressure range is from 1 to 100 pounds per square inch gage.

3. The instrument of claim 1 where the predetermined flow rate range is from 0.5 to 7 standard cubic feet per hour.

4. The instrument of claim 1 where the orifices have an area from 0.00001 to 0.0005 square inch.

5. The instrument of claim 4 where the orifices are substantially circular and have a diameter from 0.004 to 0.022 inch.

6. An instrument for analyzing a gas that is at a variable pressure elevated above atmospheric pressure, said gas flowing through the instrument to exit the instrument via a gas outlet at atmospheric pressure, said instrument comprising
a block having a sample gas inlet,
a detection cell mounted to the block past which the sample gas flows,
a scrubber attached to the block that removes unwanted substances from the sample gas prior to said sample gas flowing past the detection cell,
a valve mounted to the block, said valve having a first sample gas position that allows sample gas to flow past the detection cell and a second position that prevents sample gas from flowing past the detection cell,
a first sample gas flow path extending from the sample gas inlet through the scrubber and the valve and past the detection cell to the gas outlet, and
a second sample gas flow path in communication with the first sample gas flow path at a junction between the scrubber and the sample gas inlet and extending from said junction to the gas outlet, to divert a portion of the sample gas from flowing through scrubber and the valve and past the detection cell and to flow along said second sample gas flow path and exit the gas outlet so long as sample gas flows into the sample gas inlet at said elevated pressure,
said first and second sample gas flow paths each including a restricted orifice sized to prevent a build up of excessive pressure in the scrubber when the valve is in the second position.

7. An instrument for analyzing a gas that is at a variable pressure elevated above atmospheric pressure, said gas flowing through the instrument to exit the instrument via a gas outlet at atmospheric pressure, said instrument comprising
a block having a sample gas inlet including an orifice and a calibration gas inlet including an orifice,
a detection cell mounted to the block past which the gas being analyzed flows,
a valve mounted to the block, said valve having a closed position, a sample gas position, and a calibration gas position,
a scrubber attached to the block that removes unwanted substances from the sample gas,
a first passageway extending from the calibration gas inlet orifice through the valve and past the detection cell to the gas outlet, circumventing the scrubber,
a second passageway extending from the sample gas inlet orifice through the scrubber and the valve and past the detection cell to the gas outlet,
a third passageway in communication with the second passageway at a junction between the scrubber and the sample gas inlet orifice,
said third passageway extending from said junction to the gas outlet, circumventing the scrubber, valve and cell and enabling at least a portion of the sample gas to flow through the third passageway and exit the gas outlet so long as sample gas flows into the sample gas inlet orifice at said elevated pressure,
a bypass orifice positioned along the third passageway,
said sample gas orifice and bypass orifice being sized to maintain the pressure within the scrubber when the valve is in the closed position or the calibration gas position at a reduced pressure substantially below the elevated pressure of the gas being analyzed.

8. The instrument of claim 7 where the gas introduced through either the sample gas inlet orifice or the calibration gas orifice is within the range from 1 to 100 pounds per square inch gage, and the orifices are sized so that the flow rate of gas through the instrument is within a predetermined range from 0.5 to 7 standard cubic feet per hour.

9. The instrument of claim 8 where the orifices have an area from 0.00001 to 0.0005 square inch.

10. The instrument of claim 7 where the bypass orifice has a predetermined size that is substantially greater than the predetermined size of the sample gas inlet orifice.

11. The instrument of claim 10 where the bypass orifice and sample gas inlet orifice each have a predetermined area, and the area of the bypass orifice is at least two times greater than the area of the sample gas orifice.

12. The instrument of claim 7 where the bypass orifice has a predetermined size that is substantially less than the predetermined size of the sample gas inlet orifice.

13. The instrument of claim 12 the valve is sealed and mounted within a cavity in the side of the block, said valve having a rotary member that is manually rotated between a closed position, a sample gas position, and a calibration gas position.

14. The instrument of claim 7 where the scrubber is detachably connected to the block upstream of the detection cell and down stream of the sample gas inlet orifice and comprises a see-through container holding a removable scrubber material that removes unwanted substances and changes color to indicate that said scrubber material is exhausted and needs replacement.

15. The instrument of claim 7 including a filter between the valve and the scrubber.

16. The instrument of claim 7 including a flow meter through which gas flows.

17. The instrument of claim 7 including a heater mounted to the block.

18. The instrument of claim 17 including a thermistor mounted to the block that is a component of a control circuit for compensating for the variation in cell output with temperature.

19. An instrument for analyzing a gas including
a block having a sample gas inlet, a calibration gas inlet, and a gas outlet,
a detection cell mounted to the block past which the gas being analyzed flows, a valve mounted to the block, said valve having a closed position, a sample gas position, and a calibration gas position, a first passageway in the block extending from the calibration gas inlet through the valve and past the detection cell to the gas outlet, a second passageway in the block extending from the sample gas inlet through the valve and past the detection cell to the gas outlet, a calibration gas orifice along the first passageway upstream of the valve and detection cell, a sample gas orifice along the second passageway upstream of the valve, said sample gas orifice having a predetermined size, and a third passageway in the block, including a bypass orifice downstream of the sample gas orifice, said third passageway in communication with the gas outlet while sample gas is being introduced through the sample gas inlet when the valve is in the sample gas position, enabling at least a portion of the sample gas to flow through the third passageway and exit the gas outlet, said bypass orifice having a predetermined size that is substantially greater than the predetermined size of the sample gas orifice.

20. The instrument of claim 19 where the bypass orifice and sample gas orifice each have a predetermined area, and the area of the bypass orifice is at least two times greater than the area of the sample gas orifice.

21. The instrument of claim 19 including a scrubber attached to the block that removes from the sample gas unwanted substances.

22. The instrument of claim 21 where the scrubber is upstream of the detection cell and down stream of the sample gas orifice and comprises a see-through container holding scrubber material that removes gas unwanted substances and changes color to indicate that said scrubber material is exhausted and needs replacement.

23. The instrument of claim 22 where the container is mounted to be detached from the block to provide access to the scrubber material to replace exhausted scrubber material.

24. The instrument of claim 19 including a flow meter through which gas flows.

25. The instrument of claim 19 including a filter between the valve and the scrubber.

26. The instrument of claim 19 including a heater mounted to the block.

27. The instrument of claim 26 including a thermistor mounted to the block that is a component of a control circuit that compensates for the variation in cell output with temperature.

28. An instrument for analyzing a gas including a block having a sample gas inlet, a calibration gas inlet, and a gas outlet, a detection cell seated within a cavity in the block past which the gas being analyzed flows, a scrubber detachably connected to the block including a see-through container adapted to hold scrubber material that removes unwanted substances, said scrubber material changing colors to indicate replacement of exhausted scrubber material, a valve mounted to the block, said valve having a closed position, a sample gas position, and a calibration gas position, a first passageway in the block that bypasses the scrubber and extends from the calibration gas inlet through the valve and the detection cell to the gas outlet, a second passageway in the block having a first branch extending from the sample gas inlet through the block to a first outlet and a second branch in the block extending from a first inlet through the valve and the detection cell to the gas outlet, said scrubber being connected between the first outlet and the first inlet to enable the sample gas to flow through the scrubber prior to flowing through the valve and past the detection cell, a sample gas orifice along the first branch of the second passageway upstream of the first outlet, a third passageway placing sample gas that flows through the sample gas orifice in communication with the gas outlet at all times, enabling at least a portion of the sample gas to flow through the third passageway and exit the gas outlet, and a bypass orifice along the third passageway downstream of the sample gas orifice, said orifices being sized so that, with gas entering the instrument at an inlet orifice pressure within a predetermined range, the flow rate of gas through the instrument is within a predetermined range.

29. The instrument of claim 28 where the predetermined inlet orifice pressure range is from 1 to 100 pounds per square inch gage.

30. The instrument of claim 28 where the predetermined flow rate range is from 0.5 to 7 standard cubic feet per hour.

31. The instrument of claim 28 where the orifices have an area from 0.00001 to 0.0005 square inch.

32. The instrument of claim 31 where the orifices are substantially circular and have a diameter from 0.004 to 0.022 inch.

33. An instrument that provides a quantitative measurement of an analyte in a gas, including a detection cell that provides an indication of an amount of analyte present in the gas, a valve having a closed position, a sample gas position, and a calibration gas position, a calibration gas inlet in communication with a gas outlet through a first flow path including the valve and the detection cell, a sample gas inlet in communication with the gas outlet through a second flow path including a scrubber, the valve, and the detection cell, a sample gas orifice along the second flow path, and a bypass orifice positioned between the sample gas orifice and the gas outlet that allows at least a portion of the sample gas to exit the gas outlet, said bypass orifice being sized relative to the sample gas orifice to prevent a build up of excessive pressure within the scrubber when the valve is in the closed position or the calibration gas position.

34. The instrument of claim 33 where the sample gas orifice is always in communication with the gas outlet through the bypass orifice regardless of the position of the valve, and, with the valve in the closed position or the calibration gas position, essentially all of the sample gas exits the gas outlet, and, with the valve in the sample position, a portion of the sample gas flows past the detection cell.

35. The instrument of claim 33 where at least a portion of the sample gas exits the gas outlet as long as sample gas flows into the sample gas inlet.

36. The instrument of claim 33 where the scrubber is upstream of the detection cell and down stream of the sample gas orifice, said scrubber including a see-through container holding scrubber material that unwanted substances from the sample gas and changes color to indicate that said scrubber material is exhausted and needs replacement.

37. An instrument that provides a quantitative measurement of an analyte in a gas, including
   a block having a sample gas inlet, a calibration gas inlet, and a gas outlet,
   a detection cell within a first cavity in the block mounted to enable said cell to be removed from the cavity, said detection cell providing an indication of an amount of analyte present in gas flowing past the cell,
   a valve mounted within a second cavity in the block, said valve having rotary member that is manually moved between a closed position, a sample gas position, and a calibration gas position,
   a flow meter attached to a first external mounting section of the block, said flow meter having an entrance port and an exit port,
   a scrubber detachably connected to a second external mounting section of the block, said scrubber having an entrance port and an exit port with a container between the entrance and exit ports of said scrubber adapted to hold scrubber material that removes unwanted substances,
   said calibration gas inlet being in communication with the gas outlet through a first flow path including the valve and the detection cell,
   said sample gas inlet being in communication with the gas outlet through a second flow path including the scrubber, the valve, and the detection cell,
   a sample gas orifice in the block along the second flow path, and
   a bypass orifice in the block positioned between the sample gas orifice and the gas outlet that allows at least a portion of the sample gas to exit the gas outlet,
   said bypass orifice being sized relative to the sample gas orifice to prevent a build up of excessive pressure in the scrubber when the valve is in the closed position or the calibration gas position,
   said scrubber being upstream of the detection cell and down stream of the sample gas orifice.

38. The instrument of claim 37 where the first flow path and second flow path each include a common passageway downstream of the detection cell having a first branch that extends through the block between the detection cell and the entrance port of the flow meter and a second branch between the exit port of the flow meter and the gas outlet.

39. The instrument of claim 37 where the second flow path includes a third branch that extends through the block from the sample gas inlet through the sample gas orifice to the: entrance port of the scrubber and a fourth branch that extends through the block from the exit port of the scrubber to the valve.

40. The instrument of claim 39 where the container is made of a see-through material and it holds a scrubber material that changes color to indicate that said scrubber material is exhausted and needs replacements.

41. The instrument of claim 37 where the bypass orifice and sample gas orifice each have a predetermined area, and the area of the bypass orifice is at least two times greater than the area of the sample gas orifice.

42. The instrument of claim 37 where the block has a height of from 3 to 4 inches, a width of from 3 to 4 inches, and a depth of from 1 to 3 inches.

43. The instrument of claim 37 including a heater mounted to the block.

44. The instrument of claim 43 including a thermistor mounted to the block that that is a component of a control circuit for compensating for the variation in cell output with temperature.

45. An instrument that provides a quantitative measurement of an analyte in a gas, including
   detection cell means for providing an indication of an amount of analyte present in the gas,
   valve means for controlling the flow of gas through the instrument between a sample gas inlet or a calibration gas inlet and a gas outlet, said valve means having a closed position, a sample gas position, and a calibration gas position,
   a first flow path including the valve means and the detection cell means for placing the calibration gas inlet in communication with the gas outlet,
   a second flow path including the valve means and the detection cell means for placing the sample gas inlet in communication with the gas outlet,
   a sample gas orifice along the second flow path, and
   a bypass orifice positioned between the sample gas orifice and the gas outlet that allows at least a portion of the sample gas to exit the gas outlet at all times,
   said orifices being sized so that, with gas entering the instrument at an inlet orifice pressure within a predetermined range, the flow rate of gas through the instrument is within a predetermined range.

46. The instrument of claim 45 where at least a portion of the sample gas always exits the gas outlet as long as sample gas flows into the sample gas inlet at a pressure greater than the pressure at the gas outlet, the inlet orifice pressure varying within the range from 1 to 100 pounds per square inch gage, and the flow rate being in the range from 0.5 to 7 standard cubic feet per hour, and the orifices having an area from 0.00001 to 0.0005 square inch.

47. The instrument of claim 45 where
   with the valve in the closed position or the calibration gas position, essentially all of the sample gas exits the gas outlet, and,
   with the valve in the sample position, a portion of the sample gas flows past the detection cell.

48. The instrument of claim 45 including a scrubber upstream of the detection cell means and down stream of the sample gas orifice.

49. An instrument that provides a quantitative measurement of an analyte in a gas, including
   a block having a sample gas inlet, a calibration gas inlet, and a gas outlet,
   a scrubber connected to the block,
   a detection cell within a first cavity in a side of the block mounted to enable said cell to be removed from the cavity, said detection cell providing an indication of an amount of analyte present in the gas upon contact with the cell,
   a sealed valve mounted within a second cavity in said side of the block, said valve having rotary member that is manually rotated between a closed position, a sample gas position, and a calibration gas position,
   said second cavity having a face surface including a first opening placing the calibration gas inlet in communication with the detection cell and a second opening placing the sample gas inlet in communication with the scrubber, said rotary member, when in the sample gas position, covering the first opening to prevent communication between the calibration gas inlet and the detection cell and, when in the calibration gas position, covering the second opening to prevent communication between the sample gas inlet and the scrubber.

50. The instrument of claim 49 including a sample gas orifice and a bypass orifice positioned between the sample gas orifice and the gas outlet that allows a portion of the sample gas to exit the gas outlet at all times, said bypass orifice being sized relative to the sample gas orifice to prevent a build up of excessive pressure in the scrubber when the valve is in the closed position or the calibration gas position.

51. The instrument of claim 49 where the bypass orifice and sample gas orifice each have a predetermined area sized so that, with gas entering the instrument at an inlet orifice pressure within a predetermined range, the flow rate of gas through the instrument is within a predetermined range.

52. An instrument that provides a quantitative measurement of an analyte in a gas, including
a block having a sample gas inlet, a calibration gas inlet, and a gas outlet,
a detection cell mounted to the block that provides an indication of an amount of analyte present in gas flowing past said cell,
a valve having a cylindrical rotary member mounted within a cylindrical cavity in the block to rotate between a closed position, a sample gas position, and a calibration gas position,
said rotary member having a side wall terminating at an inner face surface and a gas conduit extending between the rotary member's inner face surface and said rotary member's side wall, said gas conduit terminating at one end in a first opening on the rotary member's inner face surface and at another end in a second opening on said rotary member's side wall,
said cavity having a side wall terminating at a sunken face surface, said sunken face surface having therein a first aperture in communication with the detection cell through a first passageway in the block, a second aperture in communication with the scrubber through a second passageway in the block, and a third aperture in communication with the calibration gas inlet through a third passageway in the block,
said rotary member, when in the sample gas position, said rotary member's inner face surface covering the third aperture to prevent communication between the calibration gas inlet and the detection cell and, when in the calibration gas position, said rotary member's inner face surface covering the second aperture to prevent communication between the scrubber and the detection cell, and said rotary member, when in the closed position, said rotary member's inner face surface covering both the second aperture and the third aperture to prevent any gas from flowing past the detection cell.

53. The instrument of claim 52 including a sample gas orifice and a bypass orifice positioned between the sample gas' orifice and the gas outlet that allows a portion of the sample gas to exit the gas outlet at all times, said bypass orifice being sized relative to the sample gas orifice so that, with gas entering the instrument at an inlet orifice pressure within a predetermined range, the flow rate of gas through the instrument is within a predetermined range.

54. The instrument of claim 53 where the bypass orifice and sample gas orifice each have a predetermined area, and the area of the bypass orifice is at least two times greater than the area of the sample gas orifice.

55. The instrument of claim 53 including a flow meter mounted to the block downstream of the detection cell and having an exit port in communication with the gas outlet through a fourth passageway in the block that by passes the detection cell.

56. The instrument of claim 53 including seal members surrounding the second and third apertures and bear against the inner face surface of the rotary member.

57. A method of measuring the amount of analyte in a sample gas, including the steps of
(a) passing the sample gas by a detection cell mounted in a block having a plurality of passageways therein that direct the flow of gas between a gas inlet and a gas outlet,
(b) passing a calibration gas by the detection cell for calibration of said cell, said calibration gas flowing at least in part through a different passageway than the sample gas,
(c) controlling which passageway gas flows through by a valve mounted in the block and moveable between a first position when the calibration gas is to flow between the gas inlet and gas outlet and a second position when the sample gas is to flow between the gas inlet and gas outlet, and
(d) providing in the block a sample gas orifice along one passageway, and a bypass orifice in the block along another passageway positioned between the sample gas orifice and the gas outlet that allows a portion of the sample gas to exit the gas outlet when the valve is in the first position, said orifices being sized so that, with gas entering the instrument at an inlet orifice pressure within a predetermined range, the flow rate of gas through the instrument is within a predetermined range.

58. The method of claim 57 where the predetermined inlet orifice pressure range is from 1 to 100 pounds per square inch gage.

59. The method of claim 58 where the predetermined flow rate range is from 0.5 to 7 standard cubic feet per hour.

60. The method of claim 59 where the orifices have an area from 0.00001 to 0.0005 square inch.

61. The method of claim 60 where the orifices are substantially circular and have a diameter from 0.004 to 0.022 inch.

* * * * *